United States Patent [19]

Zeeck et al.

[11] Patent Number: 4,859,655
[45] Date of Patent: Aug. 22, 1989

[54] URDAMYCIN G AND DERIVATIVES THEREOF, A PROCESS FOR THEIR PREPARATION AND THEIR USE

[75] Inventors: Axel Zeeck; Thomas Ciesiolka; Jürgen Rohr, all of Göttingen; Hans Zähner, Tübingen; Hannelore Drautz, Mössingen, all of Fed. Rep. of Germany

[73] Assignee: Hoechst Aktiengesellschaft, Frankfurt am Main, Fed. Rep. of Germany

[21] Appl. No.: 89,434

[22] Filed: Aug. 26, 1987

[30] Foreign Application Priority Data

Aug. 28, 1986 [DE] Fed. Rep. of Germany ....... 3629274

[51] Int. Cl.$^4$ .................... C07H 15/24; A61K 31/71; A61K 45/05; C12P 19/56
[52] U.S. Cl. ........................................ 514/34; 514/25; 536/6.4; 536/16.8; 435/78; 435/896
[58] Field of Search .................. 514/34, 25; 536/16.8, 536/6.4; 435/78, 896

[56] References Cited

FOREIGN PATENT DOCUMENTS 0257629 3/1988 European Pat. Off. .
3441933A1 6/1986 Fed. Rep. of Germany .

OTHER PUBLICATIONS

English translation of application HOE84/F 277 which corresponds to DE 3441933 A1.

Primary Examiner—Herbert J. Lilling
Attorney, Agent, or Firm—Finnegan, Henderson, Farabow, Garrett, & Dunner

[57] ABSTRACT

A new substance, urdamycin G, has been found which, like its O-acyl derivatives, exhibits an antibiotic or antitumoral activity.

11 Claims, No Drawings

URDAMYCIN G AND DERIVATIVES THEREOF, A PROCESS FOR THEIR PREPARATION AND THEIR USE

DESCRIPTION

Urdamycins A to F and their aglycones, the corresponding urdamycinones, are described in German Offenlegungsschrift 3,441,933. Urdamycins are prepared by fermentation with a microorganism strain which has been isolated from a soil sample from Tanzania. The microorganism has been identified as *Streptomyces fradiae* and filed in the Deutsche Sammlung von Microorganism (DSM) [German Register of Microorganisms] under the number DSM 3093. The corresponding urdamycinones can be obtained by acid hydrolysis or methanolysis of urdamycins.

The known urdamycins and urdamycinones have an antibacterial and tumor-inhibiting action and can therefore be used in the form of pharmaceutical preparations for treatment of bacterial infections or for treatment in tumor disorders in humans and animals.

It has been observed that the composition of the mixture of urdamycins A to F depend on the culture conditions of the microorganism. Thus, when a nutrient medium comprising full-fat soya (2%) and glucose (2%) is used, urdamycin A is formed as the major product (65%), whereas urdamycin A production is largely suppressed and urdamycin C and urdamycin D are formed as the major products when MES (morpholinoethanesulfonic acid) buffer is added to this nutrient medium. Urdamycin E is the major product (53%) when a meat extract and glucose nutrient medium (20% each) is used. Urdamycin B is produced as a major product when full-fat soya (2%), glucose (1%), starch (1%) and $NaHPO_4$ (1%) were used as the nutrient medium.

It has now been found that urdamycin G can likewise be prepared using *Streptomyces fradiae*. Here too, the yields are fermentation-dependent. Like the known urdamycins, the novel compound and its acyl derivatives have an antibacterial and tumor-inhibiting action. The acyl derivatives, in particular, even exhibit a greater activity.

The invention thus relates to:

1. The compound of the general formula I,

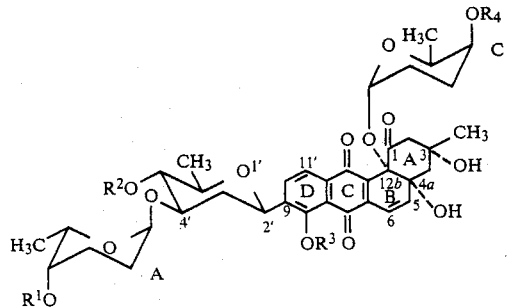

in which $R^1$-$R^4$, independently of one another, denote hydrogen or a ($C_1$-$C_{18}$) acyl group.

2. A process for the preparation of the compound of the general formula I, wherein *Streptomyces fradiae* is fermented, and the compound of the general formula I is isolated from the culture medium and acylated, if appropriate.

3. The use of the compound of the general formula I for the preparation of medicaments.

The invention, in particular with its preferred embodiments, is described below and defined in the patent claims.

*Streptomyces fradiae* is characterized as follows:
Spore surface: Sm
Spore morphology: Sa
Chromogenity: C—
Aerial mycelium color: cinnamous

*Streptomyces fradiae*, in particular the DSM 3093 strain, is employed for the fermentation. In place of DSM 3093, its mutants and variants can also be employed so long as they synthesize urdamycin G. Such mutants can be produced in a fashion which is known per se by physical means, for example irradiation, such as ultra-violet or X-ray irradiation, or chemical mutagens, such as, for example, ethyl methane sulfonate (EMS) or 2-hydroxy-4-methoxybenzophenone (MOB).

Suitable preferred carbon sources for aerobic fermentation are assimilatable carbohydrates and sugar alcohols, such as glucose, lactose or D-mannitol, and carbohydrate-containing natural products, such as malt extract. Possible preferred nitrogen-containing nutrients are: amino acids, peptides and proteins, and the degradation products thereof, such as peptones or tryptones, furthermore meat extracts, ground seeds, for example of corn, wheat, beans, soybeans or cotton plants, distillation residues from the production of alcohol, meat flours or yeast extracts, but also ammonium salts and nitrates. In addition, the nutrient solution can contain, for example, chlorides, carbonates, sulfates or phosphates of alkali metals or alkaline earth metals, iron, zinc and manganese as additional inorganic salts.

The formation of urdamycin G proceeds particularly readily in a nutrient solution which contains full-fat soya in concentrations from 0.5 to 5%, preferably 2%, and glucose in concentrations from 0.5 to 4%, preferably 2%, in each case relative to the weight of the total nutrient solution.

The fermentation takes place aerobically, i.e., for example, submersed in shaking flasks or fermenters with shaking or stirring, if appropriate while passing in air or oxygen. The fermentation can take place in a temperature range from about 18° to 40° C., preferably at about 25° to 30° C., in particular at 27° to 28° C. The microorganism is cultivated under the conditions mentioned until the stationary phase is reached, after about 60 to 80 hours, preferably 70 to 75 hours.

The cultivation is advantageously carried out in several steps, i.e. one or more preliminary cultures are initially prepared in a liquid nutrient medium, which are then inoculated into the actual production medium, the major culture, for example in the volume ratio 1:10. The preliminary culture is obtained, for example, by inoculating a spored mycelium into a nutrient solution and allowing it to grow for about 48 to 72 hours. The spored mycelium can be obtained by allowing the strain to grow for about 7 days on a solid or liquid culture medium, for example yeast-malt agar.

The fermentation process can be monitored by means of the pH of the culture or by means of the mycelium volume, by thin-layer chromatography or by testing the biological activity.

Urdamycin G is isolated from the culture medium by known methods taking into account the chemical, physical and biological properties of the products. For testing the antibiotic concentration in the culture medium or in the individual products isolated, thin-layer chromatography can be used, for example on silica gel using chloroform/methanol as eluent, the amount of antibiotic formed expediently being compared with a calibration solution.

Urdamycin G is present in the mycelium or in the culture liquor together with the known urdamycins A to F. The antibiotics can be extracted from the unfiltered culture liquor using an organic solvent which is immiscible or only sparingly miscible with water, such as chloroform or ethyl acetate. However, since they are only present in the mycelium to a minor extent, it is advantageous to separate the culture liquor from the mycelium, for example by centrifuging or filtering, preferably with addition of filtration auxiliaries.

The antibiotic can then be isolated from the supernatant or filtrate, expediently in the slightly acidic to neutral pH region, preferably at pH 6 to 7. To this purpose, organic solvents which are sparingly miscible or immiscible with water are expediently used, in particular chlorinated hydrocarbons, such as chloroform or methylene chloride, or esters, such as ethyl acetate. The colored extracts, if appropriate after evaporation and taking-up in a polar organic solvent, are freed from strongly lipophilic components, which can comprise up to about 80% of the total extract, by precipitation using a nonpolar solvent, expediently a hydrocarbon such as petroleum ether. Urdamycin G can be isolated from the residue by chromatography.

In order to isolate urdamycin G from the defeated crude extract, the latter is expediently purified via a silica gel column, mixtures of low-molecular-weight chlorinated hydrocarbons and alkanols, for example chloroform and methanol in the volume ratio 4:1 or methylene chloride and methanol in the volume ratio 85:15, having proven themselves as eluents. The components adsorbed in the form of fractions of different colors are eluted successively in the form of eluates of different colors. Urdamycin G (2nd fraction) and urdamycin A (3rd fraction, see German Offenlegungsschrift 3,441,933) are present in the two major fractions.

In order to isolate pure urdamycin G, the conventional process steps can be used, such as chromatography, gel filtration or precipitation from their solutions in suitable organic solvents. Chromatography on silica gel has proven particularly successful, a mixture of a lower halogenated hydrocarbon and a lower alkanol, for example methylene chloride/ethanol or chloroform/methanol in a volume ratio of, for example 9:1 being used as the eluent, followed by a gel filtration on suitable media, such as hydroxyalkoxypropyldextrans (lipophilic ®SEPHADEX LH brands) using a lower alkanol, such as methanol, and subsequent precipitation, for example by adding dropwise a concentrated solution of urdamycin in a polar organic solvent, such as acetone, to a nonpolar solvent, in particular a hydrocarbon, such as petroleum ether or n-hexane.

Urdamycin G is an orange, amorphous solid which is readily soluble in methanol, acetone, DMSO, dioxane and chloroform, but not in water and alkanes. In the solid state and as a solution, the substance is stable in the pH range from 3 to 9, in particular from 5 to 8, and can thus be incorporated into conventional galenic preparations.

The antibacterial action comes into effect both against Gram-positive and Gram-negative bacteria, as can be demonstrated, for example, in the plate-agar diffusion test in vitro (10 μl/test circle, 6 mm diameter).

Various bacteria which prove to be sensitive to a minimum inhibition concentration in the range from >0.03 to <0.3 μl/ml are, for example: *Achromobacter geminiani, Bacillus brevis, B. subtilis, Arthrobacter aurescens, A. crystallopoiete, Brevibacetrium flavum* and various Streptomycetes, including, for example, *S. antibioticus, S. violaceoruber, S. prasinus, S. lavendulae, glaucescens* and *S. viridochromogenes.*

It was possible to demonstrate the tumor-inhibiting action of urdamycin G on human and animal tumor cells in vitro.

Urdamycin G is converted into the corresponding ($C_1$-$C_{18}$) acyl compounds, preferably ($C_1$-$C_{10}$) acyl compounds, in particular the acetyl compound, in a fashion which is known per se using an acylating agent which introduces the desired acyl radicals of an organic carboxylic acid. The appropriate carboxylic acid or a reactive derivative, in particular an anhydride, is used here. The acylation can be carried out in the presence of suitable condensing agents, for example in the presence of carbodiimide compounds, such as dicyclohexylcarbodiimide, or carbonyl compounds, such as diimidazolylcarbonyl, when free carboxylic acids are used, and for example in the presence of basic agents, such as tri(lower alkyl)amine, for example triethylamine or heterocyclic bases, for example pyridine or 4-dimethylaminopyridine, or basic salts, for example anhydrous sodium acetate, when reactive carboxylic acid derivatives are used. The acylation reaction can be carried out in the absence or presence of a solvent or mixture of solvents with cooling, at room temperature or with warming, and, if necessary, in a closed vessel and/or in an inert gas, for example nitrogen atmosphere. Suitable solvents are, for example simple or substituted, for example chlorinated, aliphatic, cycloaliphatic or aromatic hydrocarbons, it being possible to use suitable esterification reagents, such as acetic anhydride, but also suitable bases, such as pyridine, as diluents.

However, the reaction is preferably carried out using an anhydride, in particular acetic anhydride, in the presence of pyridine or sodium acetate. The reaction temperatures and reaction times are from −10° to +100° C. and 2 minutes to 48 hours, preferably from 20° to 30° C. and 8 minutes to 16 hours. The anhydride:base ratio is in the range from 20:1 to 1:1, and is preferably 2:1. The concentration of urdamycin G in the reaction batch is between 0.05 and 10%, preferably 0.1 to 1%.

When the reaction is complete, the reaction product can be isolated by extraction. For further purification, it can then be chromatographed, for example on silica gel.

Alternatively, mono- to triacyl compounds can be prepared by basic acyl cleavage of 5′,4A,4C,8-tetra-O-acyl urdamycin G. Bases such as alkali metal or alkaline-earth metal hydroxides or alkali metal carbonates are used in aqueous/alcoholic solution at −10° to +100° C. The acyl cleavage is preferably carried out in aqueous/methanolic solution at 25° C. using a saturated sodium carbonate solution. The subsequent work-up is carried out as described above.

The acyl groups mentioned are derived from organic carboxylic acids. The latter contain straight-chain, branched or cyclic aliphatic, aliphatic-aromatic or aromatic hydrocarbon radicals which are themselves unsubstituted or substituted by halogen, for example chlorine or bromine, or esterified or etherified hydroxyl groups.

The compounds thus prepared likewise exhibit a tumor-inhibiting action.

The invention is described in detail below with reference to examples: unless otherwise stated, percentage data refer to the weight.

EXAMPLES

1. Preparation of a spore suspension of the producer strains:

(a) 100 ml of nutrient solution (4 g of yeast extract, 10 g of malt extract, 4 g of glucose and 1 liter of mains water, pH before sterilization 7.3) in a 500 ml conical flask are inoculated with the DSM 3093 strain and incbuated for 72 hours at 27° C. and 120 rpm on a rotating shaker. 20 ml of culture liquid are subsequently dispersed uniformly in a 500 ml conical flask containing the culture medium of the above mentioned composition, to which 20 g of agar/liter have been added for solidification, and the supernatant is decanted. The cultures are incubated at 27° C. for 10 to 14 days. The spores produced after this time in one flask are rinsed with 500 ml of demineralized water containing one drop of a commercially available nonionic surfactant, and used immediately or stored at −22° C.

(b) Preparation of a culture or preliminary culture of the producer strain in a conical flask.

A 500 ml conical flask containing 100 ml of a nutrient solution of the composition 2% of meat flour, 10% of malt extract, 1% of calcium carbonate and water to 100% (pH 7.2 before autoclaving) is inoculated with a culture grown in an inclined tube or with 0.2 ml of spore suspension, and is incubated on a shaker at 120 rpm and 27° C. The maximum antibiotic production is reached after 72 hours. A 48-hour-old submersed culture (5%) from the same nutrient solution is sufficient for inoculation of 10 and 100 liter fermenters.

2. Preparation of urdamycin G

A 10 liter fermenter is operated under the following conditions:

| | |
|---|---|
| Nutrient medium: | Full-fat soya 2% |
| | Glucose 2% |
| | pH 7.2 |
| Incubation time: | 72 hours |
| Incubation temperature: | 27° C. |
| Stirrer speed: | 250 rmp |
| Aeration: | 4 liters of air/min. |

The production of foam can be suppressed by repeatedly adding a few drops of ethanolic polyol solution. The production maximum is reached after about 70 hours (pH =5.3). The yields are about 40 mg of urdamycin G per liter.

3. Isolation of urdamycin G

After fermentation of DSM 3093, the culture liquor is filtered with addition of 2% of Celite as filtration auxiliary. The mycelium is extracted with acetone, the organic phase is evaporated, and the aqueous residue is extracted with ethyl acetate. The culture filtrate is likewise extracted to exhaustion at pH 7 with ethyl acetate. This extract is combined with that from the mycelium, dried and evaporated. The oily residue is covered with plenty of petroleum ether. The precipitate produced is centrifuged off and dried. The crude product is chromatographed on a silica gel column (silica gel 60, Macherey-Nagel) using methyl chloride/methanol (85:15; v:v). Urdamycin G was concentrated in fraction 2 (yellow-red) of the eluate. It was further purified on Sephadex LH 20 in methanol.

4. Characterization of urdamycin G

The purified urdamycin G is dissolved in a little acetone and precipitated by adding this solution dropwise to a 20-fold excess of n-hexane. The orange solid thus obtained decomposes at 141° C. and has the following properties:

Thin-layer chromatography: (silica gel SilG-25, UV 254+366)

Chloroform/methanol (85:15; v:v): Rf 0.44

Chloroform/methanol (9:1; v:v): Rf 0.30 neg. FAB-MS: m/e=714 (M; 12%); 664 (4%); 654 (5%); 281 (54%); 279 (46%), corresponding to $C_{37}H_{46}O_{14}$ (714.77)

IR (KBr): 3420; 2958 sh; 2910; 2840; 1718; 1650 sh; 1645 sh; 1630; 1615; 1555 $cm^{-1}$,

UV (methanol): $\nu max^{(\epsilon)}$=426.5 (4060); 319.5 (2990) nm

UV (methanol/HCl): $\lambda max^{(\epsilon)}$=430 (3950); 317 (2900) nm

UV (methanol/NaOH): $\lambda max^{(\epsilon)}$=577.2 (3800); 404 (1650); 324 (6040) nm $^1$H NMR (200 MHz, $CDCl_3$): δ=0.58 (d, J=6 Hz, 5C—$CH_3$); 1.24 (s, 3—$CH_3$); 1.24 (d, J =6 Hz, 5A—$CH_3$); approx. 1.30 (covered 3'-$H_a$); 1.43 (d, J=6 Hz, 6'—$CH_3$); 1.4-2.2 (complex, 8H, 3A—$H_2$, 2A—$H_2$, 3C—$H_2$, 2C—$CH_2$); 1.84 (d, J= 15 Hz, 4—$H_a$); 2.16 (dd, J=15; 2 Hz, 4—$H_e$); 2.46 (ddd, J=13;5;2 Hz, 3'—$H_e$); 2.52 (d. J=12.5; 2—Ha); 2.79 (dd, J=12.5;2.5 Hz, 2—$H_e$); 3.19 (dd, J=9;9 Hz, 5'—H); 3.4-3.6 (complex, 2H, 4C—H, 6'—H); 3.70 (s, broad, 4A—H); 3.72 (covered, 5C—H); 3.73 (m, 4'.H); 4.18 (dq, J=6.5;2 Hz; 5A—H); 4.88 (dd, J=11.5; 2 Hz, 2'—H); 5.01 (o, J=3×2 Hz, 1A—H); 5.40 (s, broad, 1C—H); 6.41 (d, J=10 Hz 5—H); 6.89 (d, J=10 Hz, 6—H); 7.67 (d, J=8;0.8 Hz, 11—H); 7.93 (d, J=8;0.8 Hz, 10—H); 12.33 (s, broad, OH)* ppm \* Signal disappears after $D_2O$ exchange CD (methanol): $\lambda$extr. $(\sigma^{-20} \times 10^{-3})$=401 (−9.2); 329 (21.1); 289 (10.0); 263 (−4.7); 235 (20.0) nm.

$[\alpha]_D^{20}$(c=0.1, methanol): +36°

5. Preparation of 5', 4A,4C,8-tetra-O-acetyl urdamycin G 20 mg of urdamycin G are stirred for 5.5 hours at room temperature in 12 ml of an acetic anhydride/pyridine mixture (2:1, v:v). The mixture is poured onto ice and extracted 3 times with 50 ml of chloroform in each case. The organic phase is concentrated in vacuo and traces of pyridine remaining are removed by taking-up repeatedly in toluene and evaporating. The solid residue is chromatographed on silica gel (2.5×30 cm, column, methylene chloride/ethanol 95:5; v:v). Two fractions are obtained (counted from the bottom):

1. TLC-uniform tetra-O-acetyl urdamycin G, 17 mg, yellow
2. Mixed fraction, 4 mg, yellow Tetra-O-acetyl urdamycin G is subsequently purified by chromatography on Sephadex LH 20 (2.5×50 cm, column, methanol), and 16 mg (65%) of tetra-O-acetyl urdamycin G are obtained as a yellow solid.

Thin-layer chromatography (Sil G 25, UV$_{304+366}$, 20×20 cm, 0.25 mm on glass (Macherey-Nagel), development distance 15 cm:
Chloroform/methanol (85:15, , v:v): Rf 0.70
Chloroform/methanol (9:1, v:v): Rf 0.60
C$_{45}$H$_{54}$O$_{18}$ (882.8)
Melting point 161° C.
IR (KBr): 3450; 2990; 2950; 1788; 1742; 1670; 1657 sh; 1603; 1566 cm$^{-1}$
UV (methanol): $\lambda_{max}(\epsilon) = 355$ (3060); 313 (3030); 259 (11760) nm.
$^1$H NMR (200 MHz, CDCl$_3$: $\epsilon$=0.51 (d, J=6.5 Hz, 5C—CH$_3$); 1.16 (d, J=6.5 Hz, 5A—CH$_3$); 1.26 (s, 3—CH$_3$); 1.29 (d, J=6 Hz, 6'—CH$_3$); 1.2-2.2 (complex, 12H, 2A—H$_2$, 3A—H$_2$, 3'—H$_2$, 4—H$_2$, $_2$C—H$_2$, 3C—H$_2$); 2.01; 2.11; 2.14 (3s, 5'—, 4A—and 4C—OAc); 2.49 (s, 3H, 8—OAc); 2.55 (d, J=13 Hz, 2—Ha, 2.83 (dd, J=13; 2 Hz, 2—H$_e$); 3.59 (d, J=2 Hz OH*); 3.6-3.7 (complex, 2H, 6'—H, 5C—H); 3.96 (dq, J=9.6 Hz, 5A—H); 3.98 (m, 4'—H); 4.06 (S, OH*); 4.70 (o, J=3×2 Hz, 4C—H); 4.84 (o, J=3×2 Hz, 4A—H); 4.86 (dd, J=9.9 Hz, 5'—H); 5.00 (s, broad, 1A—H) (covered, 2'—H); 5.49 (d, J=2 Hz, 1C—H); 6.42 (dd, J=10 Hz, 5—H); 6.89 (d, J=10 Hz, 6—H); 8.06 (d, J=8 Hz, 11—H); 8.15 (d, J=8 Hz, 10—H) ppm
* Signal disappears after D$_2$O exchange
CD (methanol): $\lambda$extr. ($\sigma^{-20} \times 10^{-3}$)=501 (−4.6); 450 (1.4); 394 (−12.0); 308 (−12.0); 308 (20.3); 295 sh (16.5); 266 (−11.2); 233 (25.6)nm.

6. In vitro test for cytostatic activity

The experiment was carried out in accordance with the process of Hamburger and Salmon [New Engl. J. Med. 298, 1321-1327 (1978)]. The medium was replaced by McCoy 5A, and the number of cells was reduced to 5×10$^2$ cells/plate.
(a) Action of L 1210 leukemia cells in the continuous experiment
A continuous incubation of the cells with various concentrations of the test substance from Examples 4 and 5 was carried out. The compounds to be tested were applied to the agar plates before plating-out the cell cultures. The cell cultures then grew for 5 to 7 days in the incubator in an atmosphere of 5% of CO$_2$, 20% of O$_2$ and 95% relative atmospheric humidity at 37° C. After this time, the number of cell colonies having a diameter from 60 $\mu$m was determined (in %) relative to the number of cell colonies which had grown in comparison without test substance.
(b) Action on L 1210 leukemia cells in the 1-hour experiment:
In the test, the cells were incubated at 37° C. for 1 hour at various concentrations of the test substance. The cells were then washed twice with McCoy 5A solution (Flow catalog, Meckenheim, FRG) and subsequently applied to agar plates in accordance with the method of Hamburger and Salmon. The cells were subsequently cultivated as described above, and the number of cell colonies was determined (evaluation as in a).
The IC$_{50}$ value for continuous and 1-hour incubation was determined from the dose/action curve.
(c) Proliferation experiment
L 1210 tumor cells at the exponential growth phase (5×10$^3$ cells/ml, Roswell Park Memorial Institute (RPMI) medium) were incubated in a microtiter plate with 26 recesses for a period of 72 hours at 37° C., 5% of CO$_2$ and 95% relative atmospheric humidity and various concentrations of the test substances. After 65 hours, 50 $\mu$l of [3-(4,5-dimethylthiazol-2-yl)-2,5-diphenyltetrazolium bromide](MTT) (2.5 mg/ml of MTT in phosphate buffer saline (PBS)) were added. The MTT was reduced by living cells into the red, water-insoluble dyestuff formazan. After a further 7 hours, the supernatant medium was carefully removed. Formazan was dissolved by adding 100 $\mu$l of dimethyl sulfoxide per recess and subsequent shaking gently. The extinction of each recess was determined using a Multisan 340 CC photometer (Messrs. Flow) at 492 nm. The results were determined from the extinction ratio of cells with test substance to cells without test substance.

In all cases, the experiments were carried out 4 times. The deviation in the results was less than 15%.

The results are collated in the following table:

| | IC$_{50}$ ($\mu$l/ml) | | |
| | | Soft-agar assay | |
| Test substance | Proliferation assay | continuous incubation | 1-hour incubation |
| --- | --- | --- | --- |
| Urdamycin G | 3.5 | 0.85 | |
| 5',4A,4C,8-Tetra-O—acetyl-urdamycin G | <1 | 0.036 | 0.065 |

We claim:
1. A compound of the formula I

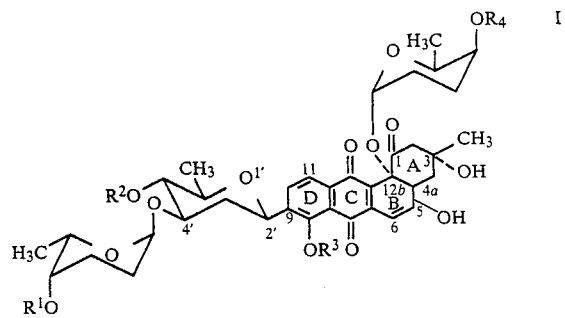

in which R$^1$ to R$^4$, independently of one another, denote hydrogen or a (C$_1$-C$_{18}$)-acyl group.

2. A compound as claimed in claim 1, in which R$^1$ to R$^4$, independently of one another, denote hydrogen or (C$_1$-C$_{10}$)-acyl.

3. A compound as claimed in claim 1, in which R$^1$ to R$^4$, independently of one another, denote hydrogen or acetyl.

4. A process for the preparation of a compound of the formula

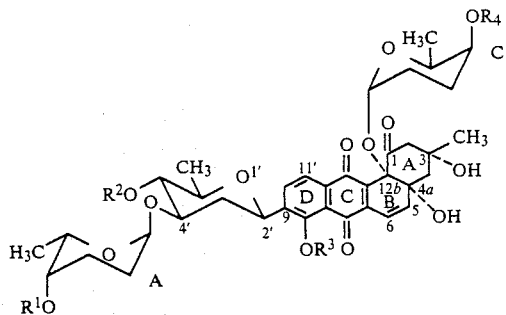

in which $R^1$ to $R^4$, independently of one another, denote hydrogen or a $(C_1-C_{18})$-acyl group, wherein
(a) *Streptomyces fradiae* is cultivated,
(b) a compound of the formula I in which $R^1$ to $R^4$ denote hydrogen is isolated, and, if appropriate,
(c) this compound is acylated.

5. The process as claimed in claim 4, wherein *Streptomyces fradiae* DSM 3093 is employed.

6. The process as claimed in claim 4, wherein *Streptomyces fradiae* is cultivated in a nutrient solution containing 0.5 to 5% of full-fat soya.

7. The process as claimed in claim 4, wherein *Streptomyces fradiae* is cultivated in a temperature range from 18° to 40° C.

8. The process as claimed in claim 7, wherein the temperature range is 25° to 30° C.

9. The process as claimed in claim 4, wherein *Streptomyces fradiae* is cultivated over a period of 40 to 80 hours.

10. The process as claimed in claim 9, wherein *Streptomyces fradiae* is cultivated for 70 to 75 hours.

11. A pharmaceutical composition comprising an effective amount of the compound as claimed in claim 1 and a pharmaceutically acceptable carrier.

* * * * *